United States Patent [19]

Bindra et al.

[11] 4,041,163

[45] Aug. 9, 1977

[54] N-(5-TETRAZOLYL)-4-OXO-4H-PYRIMIDO(2,1-B)BENZOTHIAZOLE-3-CARBOXAMIDE ANTIALLERGY AGENTS

[75] Inventors: Jasjit S. Bindra, Groton; Saul B. Kadin, New London, both of Conn.

[73] Assignee: Pfizer Inc., New York, N.Y.

[21] Appl. No.: 671,030

[22] Filed: Mar. 29, 1976

[51] Int. Cl.$^2$ ............... A61K 31/505; C07D 513/02
[52] U.S. Cl. .......................... 424/251; 260/256.5 R
[58] Field of Search ............... 260/256.5 R; 424/251

[56] References Cited

U.S. PATENT DOCUMENTS 3,538,086  11/1970  Mair et al. .............. 260/239.75

OTHER PUBLICATIONS

Chemical Abstracts, 77:164743k (1972).

*Primary Examiner*—Leonard Schenkman
*Attorney, Agent, or Firm*—Connolly and Hutz

[57] ABSTRACT

N-(5-Tetrazolyl)-4-oxo-4H-pyrimido[2,1-b]benzothiazoles and their use as antiallergy agents.

16 Claims, No Drawings

N-(5-TETRAZOLYL)-4-OXO-4H-PYRIMIDO(2,1-B)BENZOTHIAZOLE-3-CARBOXAMIDE ANTIALLERGY AGENTS

BACKGROUND OF THE INVENTION

1. Field of the Invention

This invention relates to N-(5-tetrazolyl)-4-oxo-4H-pyrimido[2,1-b]benzothiazoles and salts thereof and to their use for the control of allergic reactions.

2. Description of the Prior Art

The pyrimido[2,1-b]benzothiazole ring system was first reported by Antaki, et al., *J. Chem. Soc.*, 551 (1951). Other examples of this ring system were reported by Gompper, et al., *Chem. Ber.*, 95, 2871 (1962), Galasko, et al., *J. S. Afr. Chem. Inst.*, 22, 121 (1969), Dunwell, et al., *J. Chem. Soc.*, (C) 2094 (1971), and Alaimo, *J. Hetero. Chem.*, 10, 769 (1973).

U.S. Pat. No. 3,538,086 teaches the use of 4-oxo-4H-pyrimido[2,1-b]benzothiazoles as antiviral agents, while Richardson, et al., *J. Med. Chem.*, 15, 1203 (1972) tested similar compounds as antimicrobial agents.

Allergic reactions, the symptoms resulting from an antigen-antibody interaction, manifest themselves in a wide variety of ways and in different organs and tissues. Common allergic disorders, for example, are allergic rhinitis, a condition characterized by seasonal or perennial sneezing, running nose, nasal congestion, with itching and congestion of eyes; hay fever, a variety of allergic rhinitis that results from hypersensitivity to grass pollens; and bronchial asthma, one of the most disabling and debilitating of allergic reactions, a disease characterized by hyper-reactivity of the bronchi on exposure to various immunogenic or nonimmunogenic stimuli, resulting in bronchospasms with wheezing, short-lived paroxysms and widespread constriction of airway passages. The mechanical obstruction to airflow in airways is generally reversed by the use of bronchodilators, which provide symptomatic relief. In contrast, antiallergy agents prevent the release of mediators of anaphylaxis from tissue stores to preclude elicitation of bronchoconstriction by the mediators.

Recently, Cox and co-inventors, *Adv. in Drug Res.*, 5, 115 (1970), described the pharmacology of one such agent, disodium chromoglycate [1,3-bis-(2-carboxycromon-5-yloxy)-2-hydroxypropane, Intal]. It is not a bronchodilator, but mediates its therapeutic effects by a unique mechanism of action involving inhibition of release of mediators of anaphylaxis and is administered prophylactically. It suffers from lack of oral efficacy and, for optimum results, is administered by inhalation as a solid inhalant. Further, although it is effective against anaphylaxis due to immunoglobulin E (IgE), it is effective against anaphylaxis due to immunoglobulin G (IgG) only at high doses (60–70% protection at 100 and 300 mg./kg.).

Although the aforementioned agents represent outstanding contributions toward the treatment of asthma, many of them exert the undesired side effect of cardiac stimulation.

SUMMARY OF THE INVENTION

It has now been found that N-(5-tetrazolyl)-4-oxo-4H-pyrimido[2,1-b]benzothiazole-3-carboxamides of the formula:

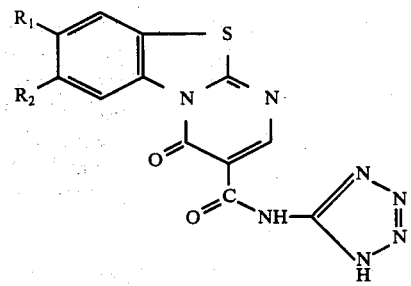

and the pharmaceutically acceptable base salt thereof, wherein $R_1$ is hydrogen, alkyl of 1 to 3 carbon atoms, alkoxy of 1 to 3 carbon atoms, hydroxy, chloro, fluoro, trifluoromethyl, nitro, amino or methylthio; $R_2$ is hydrogen, alkyl of 1 to 3 carbon atoms, alkoxy of 1 to 3 carbon atoms, hydroxy, chloro, fluoro, or methylthio; and $R_1$ and $R_2$ when taken together are methylenedioxy or ethylenedioxy, are valuable antiallergy agents; that is, agents which inhibit the release of mediators of anaphylaxis, in mammals, including man, and in this way reduce the tendency of bronchoconstriction by the mediators. They are not bronchodilators. They are, in contrast to Intal, of practical value against both IgG and IgE mediated anaphylaxis when administered via the oral and intraperitoneal routes of administration, and by inhalation.

Compounds of the above formula of special interest because of their significant oral activity in the PCA test against both IgG and IgE are those wherein $R_1$ is alkoxy having 1 to 3 carbon atoms. A second preferred group of compounds are those wherein $R_2$ is hydrogen.

The antiallergy property of the compounds of this invention is evaluated by the passive cutaneous anaphylaxis (PCA) test (Ovary, *J. Immun.*, 81, 355, 1958). In the PAC test normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

DETAILED DESCRIPTION OF THE INVENTION

The compounds of the present invention are conveniently prepared by acylating 5-aminotetrazole with an appropriately substituted 3-carboxy-4-oxo-4H-pyrimido[2,1-b]benzothiazole. This acylation is achieved by contacting the reactants in about equimolar quantities. In practice it is preferred that an excess of 10–20% of the aminotetrazole be employed.

Since the condensation of a carboxyl group with an amino function is not a facile reaction, it is necessary to activate the 3-carboxy group. This transformation is carried out by first reacting the 3-carboxy-4-oxo-4H-pyrimido-[2,1-b]benzothiazole with 1,1-carbonyldiimidazole. The resulting imidazolide, which is generated in situ, is then allowed to react with the aminotetrazole. The uses of 1,1-carbonyldiimidazole are reviewed by Staub, *Angew. Chem. Internat. Ed.,* 1, 351 (1962).

The reaction is carried out in a reaction-inert solvent. By such a solvent is meant one which does not react appreciably with the reactants or product, and solubilizes said reactants to an appreciable extent. The preferred type of solvents for this reaction are highly polar, aprotic solvents, such as hexamethylphosphoramide, dimethylsulfoxide, dimethylformamide and dimethylacetamide. The especially preferred solvent is dimethylformamide.

Reaction time is not critical and is dependent on reaction temperature, concentration of reactants and their relative reactivity. When steam bath temperatures are employed, the reaction to form the activated imidazolide requires a 10–15 min. reaction time, while the reaction of the activated imidazolide with 5-aminotetrazole requires 20–60 min. Longer reaction times are required when lower reaction temperatures are employed.

The reagents 5-aminotetrazole and 1,1'-carbonyldiimidazole are readily available commercially or can be prepared from literature procedures. The 3-carboxy-4-oxo-4H-pyrimido[2,1-b]benzothiazoles are prepared according to the procedure of Alaimo, *J. Hetero. Chem.,* 10, 769 (1973).

As has been previously noted, a characteristic feature of the acidic compounds of the instant invention is their ability to form basic salts. Acid congeners of the present invention are converted to basic salts by the interaction of said acid with an appropriate base in an aqueous or nonaqueous medium. Such basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, secondary amines such as dicyclohexylamine and tertiary amines such as diethylaniline, N-methylpyrrolidine and N-methylmorpholine; sodium hydroxide, potassium hydroxide, ammonium hydroxide, sodium ethoxide, potassium methoxide, magnesium hydroxide, calcium hydride and barium hydroxide.

The preferred antiallergy agents and their basic salts are N-(5-tetrazolyl)-7,8-dimethoxy-4-oxo-4H-pyrimido[2,1-b]benzothiazole-3-carboxamide, N-(5-tetrazolyl)-7,8-diethoxy-4-oxo-4H-pyrimido[2,1-b]benzothiazole-3-carboxamide, N-(5-tetrazolyl)-7-methoxy-4-oxo-4H-pyrimido[2,1-b]benzothiazole-3-carboxamide, N-(5-tetrazolyl)-7-fluoro-4-oxo-4H-pyrimido[2,1-b]benzothiazole-3-carboxamide and N-(5-tetrazolyl)-4-oxo-4H-pyrimido[2,1-b]benzothiazole-3-carboxamide.

The products of this invention and the pharmaceutically acceptable basic salts thereof are useful as prophylactic agents to inhibit or prevent the release of mediators of anaphylaxis (allergy, immediate hypersensitivity reactions) and the occurrence of allergic symptoms in mammals, and can be administered for such uses individually or as mixtures with other agents; for example, with theophylline or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds in sesame or peanut oil or aqueous propylene glycol solutions can be employed, as well as sterile aqueous solutios of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

Having full regard for the foregoing factors, it is considered that an effective daily oral or intraperitoneal dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively inhibit or prevent release of mediators of anaphylaxis in human subjects. These values are illustrative and there may, of course, be individual cases where higher or lower dose ranges are merited. With careful supervision, the dosage level can range up to as high as about 2 grams per day.

When administered intravenously or by inhalation, the effective daily dose is from about 0.05 to about 400 mg. per day, and preferably from about 0.25 to 200 mg. per day, or at about 0.005 to 4 mg./kg. of body weight in a single or divided dose.

When used as prophylactic agents to prevent the release of mediators of anaphylaxis, the compounds can be administered by inhalation. Compositions suitable for inhalation can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for administration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent of from about 1:0.5 to about 1:1.5.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The PCA test is a measure of the anti-allergic (especially anti-asthmatic) activity of a compound. Compounds which inhibit a positive PCA test induced by the rat immunochemical counterpart of human immunoglobulin E (IgE), or reagin, are considered to have anti-allergic activity (C. Mota, Ann. N.Y. Acad. Sci., 103, 264 1963). (Reagin is primarily immunoglobulin E [IgE]and is the principal immunoglobulin responsible for allergic asthma, anaphylaxis, hay fever, food sensitivities and certain manifestations of drug sensitivities, although recent evidence ascribes to the IgG class of antibodies a significant role in the mediation of allergic diseases). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions of a reagin mediated nature.

To put it another way, such compounds block the release of mediators resulting from the antigen-antibody (allergic) reaction as illustrated in the PCA test using rat homocytotropic antibody—a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170–210 g. Reaginic antiserum, rich in IgE antibodies, is prepared according to Petillo et al., Int. Arch. Allergy, 44, 309 (1973). Hyperimmune antiserum rich in IgG antibodies to hen egg albumin is prepared according to Orange et al., J. Exptl. Med., 127, 767 (1968). Forty-eight hours prior to antigen challenge, the reaginic antiserum is injected intradermally (i.d.) into the shaved skin of a normal rat's back; 5 hours before challenge the hyperimmune antisera is similarly injected. At a third site 60 mcg. histamine dihydrochloride and 0.5 mcg. serotonin creatinine sulfate are injected i.d. just prior to antigen challenge as a check for antihistaminic, antiserotonin and unspecific types of blockage; the compounds of the instant invention or saline are then administered i.v. and immediately followed by the challenge of 5 mg. egg albumen and 2.5 mg. Evans' Blue dye in saline. In the case of oral administration Evans' Blue dye and egg albumin are given 5 minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of five animals and compared to the saline treated controls. The difference is expressed as percent blockage due to the compound employed.

Compounds representative of those of the present invention are tested for antiallergy activity by the above-described procedure and the resulting activities are reported as the degree (%) of protection. Intal, disodium cromoglycate, a commercial antiallergy agent, is included for comparison.

The compounds tested are of the formula:

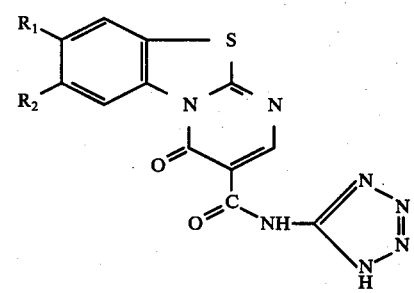

Activity of compounds administered orally or intravenously are indicated in Table I and II, respectively.

TABLE I

| | | IgE I.V. mg./kg. | | | | | IgG I.V. mg./kg. | | | | |
| --- | --- | --- | --- | --- | --- | --- | --- | --- | --- | --- | --- |
| $R_1$ | $R_2$ | 0.01 | 0.03 | 0.1 | 0.3 | 3.0 | 0.01 | 0.03 | 0.1 | 0.3 | 3.0 |
| $CH_3$- | $CH_3$- | | | | | 80 | | | | | 34 |
| $CH_3O$- | H- | | 100 | | | | | 55 | | | |
| F- | H- | | 53 | | | | | 41 | | | |
| Cl- | H- | | | | 78 | 100 | | | | 23 | 84 |
| $CH_3$- | H- | | | | 90 | | | | | 60 | |
| $CH_3O$- | $CH_3O$- | | | 100 | | | | | 85 | | |
| $C_2H_5O$- | $C_2H_5O$- | | | 100 | | | | | 87 | | |
| H- | H- | 48 | | | | | 54 | | | | |
| | Intal | | | | 29 | | | | 78 | | |

TABLE II

| R₁ | R₂ | IgE P.O. mg./kg. 0.1 | 1.0 | 3.0 | IgG P.O. mg./kg. 0.1 | 1.0 | 3.0 |
|---|---|---|---|---|---|---|---|
| CH₃O- | H- | 85 | | | 57 | | |
| Cl- | H- | | 100 | | | | 84 |
| CH₃O- | CH₃O- | | 79 | | | 45 | |
| H- | H- | 72 | | | 59 | | |

The following examples are provided solely for the purpose of illustration and are not to be construed as limitations of this invention, many variations of which are possible without departing from the spirit or scope thereof.

EXAMPLE 1

N-(5-Tetrazolyl)-4-oxo-4H-pyrimido[2,1-b]benzothiazole-3-carboxamide

To a solution of 360 mg. of 1,1′-carbonyldiimidazole in 6 ml. of dry tetrahydrofuran at 140° C. is added dropwise 500 mg. of 3-carboxy-4-oxo-4H-pyrimido[2,1-b]benzothiazole in 6 ml. of dry dimethylformamide. After heating for 3 hrs., 186 mg. of 5-aminotetrazole is added, and the heating maintained for an additional 15 min. The reaction mixture is cooled and the precipitated product filtered. Recrystallization from dimethylformamide gives 200 mg. of the desired product, m.p. 330°–332° C.

Anal. Calc'd. for $C_{12}H_7O_2N_7S$: C, 46.0; H, 2.3; N, 31.3. Found: C, 45.9; H, 2.4; N, 31.6.

EXAMPLE 2

N-(5-Tetrazolyl)-7-methyl-4-oxo-4H-pyrimido[2,1-b]benzothiazole-3-carboxamide

A slurry of 1.2 g. of 3-carboxy-7-methyl-4-oxo-4H-pyrimido[2,1-b]benzothiazole and 827 mg. of 1,1-carbonyldiimidazole is heated on a steam bath for 15 min. Without removing the clear solution from the heat source, 434 mg. of 5-aminotetrazole is added, and the heating continued for 30 min. The reaction mixture is cooled, and the resulting precipitate is filtered and washed with a small amount of water. Drying provided 1.2 g. of the desired product as a white solid, m.p. >300° C.

Anal. Calc'd. for $C_{13}H_9O_2N_7S$: C, 47.7; H, 2.8; N, 30.0. Found: C, 48.1; H, 3.0; N, 29.8.

EXAMPLE 3

N-(5-Tetrazolyl)-7-methoxy-4-oxo-4H-pyrimido[2,1-b]benzothiazole-3-carboxamide

To a suspension of 829 mg. of 3-carboxy-7-methoxy-4-oxo-4H-pyrimido[2,1-b]benzothiazole is added 535 mg. of 1,1′-carbonyldiimidazole and the suspension heated to 90° C. on a steam bath. After heating for 15 min. 281 mg. of 5-aminotetrazole is added and the heating continued for 20 min. The mixture is cooled and the precipitated solid, which commences to form during the heating period, is filtered, 750 mg., m.p. > 300° C. Recrystallization from dimethylformamide gives 590 mg. of the purified product, m.p. > 300° C.

Anal. Calc'd. for $C_{13}H_9O_3N_7S$: C, 45.5; H, 2.6; N, 28.6. Found: C, 45.6; H, 2.7; N, 28.4.

Starting with 5-aminotetrazole and the appropriately substituted 3-carboxy-4-oxo-4H-pyrimido[2,1-b]benzothiazole, and employing the procedure of Examples 1–3, the following amides are synthesized: N-(5-tetrazolyl)-7-ethoxy-4-oxo-4H-pyrimido[2,1-b]benzothiazole-3-carboxamide; N-(5-tetrazolyl)-7-n-propoxy-4-oxo-4H-pyrimido[2,1-b]benzothiazole-3-carboxamide; N-(5-tetrazolyl)-7-i-propoxy-4-oxo-4H-pyrimido[2,1-b]benzothiazole-3-carboxamide; N-(5-tetrazolyl)-7-ethyl-4-oxo-4H-pyrimido[2,1-b]benzothiazole-3-carboxamide; N-(5-tetrazolyl)-7-i-propyl-4-oxo-4H-pyrimido[2,1-b]benzothiazole-3-carboxamide; N-(5-tetrazolyl)-8-methoxy-4-oxo-4H-pyrimido[2,1-b]benzothiazole-3-carboxamide; N-(5-tetrazolyl)-8-n-propoxy-4-oxo-4H-pyrimido[2,1-b]benzothiazole-3-carboxamide; N-(5-tetrazolyl)-8-ethyl-4-oxo-4H-pyrimido[2,1-b]benzothiazole-3-carboxamide; and N-(5-tetrazolyl)-8-i-propyl-4-oxo-4H-pyrimido[2,1-b]benzothiazole-3-carboxamide.

EXAMPLE 4

N-(5-Tetrazolyl)-7-fluoro-4-oxo-4H-pyrimido[2,1-b]benzothiazole-3-carboxamide

To a solution of 1.3 g. of 3-carboxy-7-fluoro-4-oxo-4H-pyrimido[2,1-b]benzothiazole in 50 ml. of dimethylformamide is added 892 mg. of 1,1′-carbonyldiimidazole, and the reaction heated at steam bath temperatures for 15 min. Without removing the resulting solution from the steam bath, 468 mg. of 5-aminotetrazole is added and the heating continued for 20 min. The mixture is cooled and the precipitated product is filtered, washed with water and dried, 1.06 g., m.p. > 300° C.

Anal. Calc'd. for $C_{12}H_6O_2N_7FS$: C, 43.5; H, 1.8; N, 29.6. Found: C, 43.5; H, 2.1; N, 29.3.

EXAMPLE 5

N-(5-Tetrazolyl)-7-chloro-4-oxo-4H-pyrimido[2,1-b]benzothiazole-3-carboxamide

In a manner similar to Example 4, 1.4 g. of 3-carboxy-7-chloro-4-oxo-4H-pyrimido[2,1-b]benzothiazole is reacted with 892 mg. of 1,1′-carbonyldiimidazole in 60 ml. of dimethylformamide at steam bath temperatures for 15 min. 5-Aminotetrazole (468 mg.) is added and the reaction mixture is heated for 30 min. The resulting suspension is cooled and filtered, 1.5 g., m.p. > 300° C.

Anal. Calc'd. for $C_{12}H_6O_2N_7ClS$: C, 41.4; H, 1.7; N, 28.2. Found: C, 41.7; H, 2.1; N, 27.8.

EXAMPLE 6

The general procedure of Examples 4 and 5 is repeated, starting with the requisite 3-carboxy-4-oxo-4H-pyrimido[2,1-b]benzothiazole, 5-aminotetrazole and 1,1′-carbonyldiimidazole, to provide the following products:

N-(5-tetrazolyl)-7-trifluoromethyl-4-oxo-4H-pyrimido[2,1-b]benzothiazole-3-carboxamide; N-(5-tetrazolyl)-7,8-dichloro-4-oxo-4H-pyrimido[2,1-b]-benzothiazole-3-carboxamide; N-(5-tetrazolyl)-7,8-difluoro-4-oxo-4H-pyrimido[2,1-b]benzothiazole-3-carboxamide; N-(5-tetrazolyl)-8-fluoro-4-oxo-4H-pyrimido[2,1-b]benzothiazole-3-carboxamide; N-(5-tetrazolyl)-8-chloro-4-oxo-4H-pyrimido[2,1-b]benzothiazole-3-carboxamide; N-(5-tetrazolyl)-7-trifluoromethyl-8-fluoro-4-oxo-4H-pyrimido[2,1-b]benzothiazole-3-carboxamide; N-(5-tetrazolyl)-7-fluoro-8-chloro-4-oxo-4H-pyrimido[2,1-b]benzothiazole-3-carboxamide; and N-(5-tetrazolyl)-7-chloro-8-fluoro-4-oxo-4H-pyrimido[2,1-b]benzothiazole-3-carboxamide.

EXAMPLE 7

N-(5-Tetrazolyl)-7,8-dimethyl-4-oxo-4H-pyrimido[2,1-b]benzothiazole-3-carboxamide To a suspension of 2.0 g. of 3-carboxy-4-oxo-4H-pyrimido[2,1-b]benzothiazole in 125 ml. of dimethylformamide is added 1.3 g. of 1,1'-carbonyldiimidazole, and the resulting solution heated on a steam bath until the evolution of gas ceases (20 min.). 5-Aminotetrazole (680 mg.) is added and the heating continued for 1 hr. The resulting suspension is cooled and filtered, 1.8 g., m.p. > 300° C.

Anal. Calc'd. For $C_{14}H_{11}O_2N_7S$: C, 49.3; H, 3.3; N, 28.7. Found: C, 49.8; H, 3.3; N, 28.0.

EXAMPLE 8

The procedure of Example 7 is repeated, starting with the appropriate reagents, to provide the following analogs:

N-(5-tetrazolyl)-7,8-diethyl-4-oxo-4H-pyrimido[2,1-b]benzothiazole-3-carboxamide; N-(5-tetrazolyl)-7,8-di-n-propyl-4-oxo-4H-pyrimido[2,1-b]benzothiazole-3-carboxamide; N-(5-tetrazolyl)-7,8-di-i-propyl-4-oxo-4H-pyrimido[2,1-b]benzothiazole-3-carboxamide; N-(5-tetrazolyl)-7-methyl-8-n-propyl-4-oxo-4H-pyrimido[2,1-b]benzothiazole-3-carboxamide; and N-(5-tetrazolyl)-7-n-propyl-8-methyl-4-oxo-4H-pyrimido[2,1-b]benzothiazole-3-carboxamide.

EXAMPLE 9

N-(5-Tetrazolyl)-7-methyl-8-chloro-4-oxo-4H-pyrimido[2,1-b]benzothiazole-3-carboxamide To 115 ml. of dimethylacetamide is added 1.8 g. of 3-carboxy-4-oxo-4H-pyrimido[2,1-b]benzothiazole followed by 1.3 g. of 1,1'-carbonyldiimidazole, and the resulting mixture heated on a steam bath for 15 min. 5-Aminotetrazole (680 mg.) is added and the heating continued for 35 min. The suspension is cooled, filtered, and the solids washed with water. An analytical sample of the desired product is recrystallized from a large volume of dimethylformamide.

EXAMPLE 10

Following the procedure of Example 9, and employing the requisite starting reagents, the indicated compounds are prepared.

| $R_1$ | $R_2$ |
|---|---|
| CH$_3$- | F- |
| C$_2$H$_5$- | Cl- |
| C$_2$H$_5$- | F- |
| n-C$_3$H$_7$- | Cl- |
| CF$_3$- | CH$_3$- |
| CF$_3$- | i-C$_3$H$_7$- |
| Cl- | CH$_3$- |
| F- | C$_2$H$_5$- |
| Cl- | n-C$_3$H$_7$- |

EXAMPLE 11

N-(5-Tetrazolyl)-7,8-dimethoxy-4-oxo-4H-pyrimido[2,1-b]benzothiazole-3-carboxamide A slurry of 1.5 g. of 3-carboxy-4-oxo-4H-pyrimido[2,1-b]benzothiazole and 892 mg. of 1,1'-carbonyldiimidazole in 60 ml. of dimethylformamide is heated at steam bath temperatures for 10 min. 5-Aminotetrazole (468 mg.) is added, and the heating continued for 15 min. The resulting suspension is cooled and filtered. The solids are recrystallized from dimethylformamide, 970 mg., m.p. > 300° C.

Anal. Calc'd. for $C_{14}H_{11}O_4N_7S$: C, 45.0; H, 3.0; N, 26.3. Found: C, 45.0; H, 3.1; N, 25.6.

EXAMPLE 12

N-(5-Tetrazolyl)-7-methylthio-4-oxo-4H-pyrimido[2,1-b]benzothiazole-3-carboxamide A suspension containing 1.34 g. of 3-carboxy-4-oxo-4H-pyrimido[2,1-b]benzothiazole and 827 mg. of 1,1'-carbonyldiimidazole in 50 ml. of dimethylformamide is heated on a steam bath for 20 min. The resulting solution is treated with 434 mg. of 5-aminotetrazole and the heating continued for 20 min. The suspension is cooled and filtered. The desired product can be further purified by recrystallization from dimethylformamide.

EXAMPLE 13

Employing the procedure of Example 12 and starting with the appropriate reagents, the following compounds are prepared:

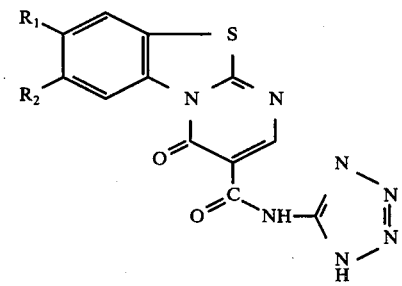

| $R_1$ | $R_2$ |
|---|---|
| CH$_3$S- | CH$_3$S- |
| CH$_3$S- | Cl- |
| CH$_3$S- | F- |
| CH$_3$S- | CH$_3$- |
| CH$_3$S- | n-C$_3$H$_7$- |
| CH$_3$S- | CH$_3$O- |
| CH$_3$S- | C$_2$H$_5$O- |

EXAMPLE 14

The procedure of Example 12 is again repeated, starting with the requisite reagents, to provide the following products:

N-(5-tetrazolyl)-7-methyl-8-methylthio-4-oxo-4H-pyrimido[2,1-b]benzothiazole-3-carboxamide; N-(5-tetrazolyl)-7-ethyl-8-methylthio-4-oxo-4H-pyrimido[2,1-b]benzothiazole-3-carboxamide; N-(5-tetrazolyl)-7-methoxy-8-methylthio-4-oxo-4H-pyrimido[2,1-b]benzothiazole-3-carboxamide; N-(5-tetrazolyl)-7-n-propoxy-8-methylthio-4-oxo-4H-pyrimido[2,1-b]benzothiazole-3-carboxamide; N-(5-tetrazolyl)-7-chloro-8-methylthio-4-oxo-4H-pyrimido[2,1-b]benzothiazole-3-carboxamide; N-(5-tetrazolyl)-7-fluoro-8-methylthio-4-oxo-4H-pyrimido[2,1-b]benzothiazole-3-carboxamide; and N-(5-tetrazolyl)-7-trifluoromethyl-8-methylthio-4-oxo-4H-pyrimido[2,1-b]benzothiazole-3-carboxamide.

EXAMPLE 15

N-(5-Tetrazolyl)-7-nitro-4-oxo-4H-pyrimido[2,1-b]benzothiazole-3-carboxamide

3-Carboxy-7-nitro-4-oxo-4H-pyrimido[2,1-b]benzothiazole (1.34 g.) and 827 mg. of 1,1'-carbonyldiimidazole are added to 60 ml. of dimethylacetamide, and the suspension heated on a steam bath for 15 min. To the resulting solution is added 434 mg. of 5-aminotetrazole and the heating continued for 20 min. The suspension is cooled and filtered. The desired product can be further purified by recrystallization from dimethylformamide.

EXAMPLE 16

Starting with the appropriately substituted 3-carboxy-4-oxo-4H-pyrimido[2,1-b]benzothiazole, 5-aminotetrazole and carbonyldiimidazole and employing the procedure of Example 15, the following compounds are prepared:
N-(5-tetrazolyl)-7-nitro-8-methylthio-4-oxo-4H-pyrimido[2,1-b]benzothiazole-3-carboxamide; N-(5-tetrazolyl)-7-nitro-8-methyl-4-oxo-4H-pyrimido[2,1-b]benzothiazole-3-carboximide; N-(5-tetrazolyl)-7-nitro-8-n-propyl-4-oxo-4H-pyrimido[2,1-b]benzothiazole-3-carboxamide; N-(5-tetrazolyl)-7-nitro-8-methoxy-4-oxo-4H-pyrimido[2,1-b]benzothiazole-3-carboxamide; N-(5-tetrazolyl)-7-nitro-8-ethoxy-4-oxo-4H-pyrimido[2,1-b]benzothiazole-3-carboxamide; N-(5-tetrazolyl)-7-nitro-8-hydroxy-4-oxo-4H-pyrimido[2,1-b]benzothiazole-3-carboxamide; N-(5-tetrazolyl)-7-nitro-8-chloro-4-oxo-4H-pyrimido[2,1-b]benzothiazole-3-carboxamide; and N-(5-tetrazolyl)-7-nitro-8-fluoro-4-oxo-4H-pyrimido[2,1-b]benzothiazole-3-carboxamide.

EXAMPLE 17

N-(5-Tetrazolyl)-7-amino-4-oxo-4H-pyrimido[2,1-b]benzothiazole-3-carboxamide

To a suspension of 4.5 g. of N-(5-tetrazolyl)-7-nitro-4-oxo-4H-pyrimido[2,1-b]benzothiazole-3-carboxamide in 50 ml. of water and 25 ml. of dimethylformamide is added sufficient 1N aqueous sodium hydroxide to effect a solution. Platinum oxide (300 mg.) is added and the suspension shaken in a hydrogen atmosphere at an initial pressure of 30 p.s.i. When the theoretical amount of hydrogen is absorbed the spent catalyst is filtered and the filtrate treated with sufficient 6N hydrochloric acid to register acid to Congo red paper. The acidified filtrate is further diluted with 25 ml. of water and cooled in an ice bath. The desired product is filtered and recrystallized from dimethylformamide.

EXAMPLE 18

Starting with the appropriate pyrimido[2,1-b]benzothiazole from Example 16, and employing the procedure of Example 17, the following compounds are prepared:
N-(5-tetrazolyl)-7-amino-8-methylthio-4-oxo-4H-pyrimido[2,1-b]benzothiazole-3-carboxamide; N-(5-tetrazolyl)-7-amino-8-methyl-4-oxo-4H-pyrimido[2,1-b]benzothiazole-3-carboxamide; N-(5-tetrazolyl)-7-amino-8-n-propyl-4-oxo-4H-pyrimido[2,1-b]benzothiazole-3-carboxamide; N-(5-tetrazolyl)-7-amino-8-methoxy-4-oxo-4H-pyrimido[2,1-b]benzothiazole-3-carboxamide; N-(5-tetrazolyl)-7-amino-8-ethoxy-4-oxo-4H-pyrimido[2,1-b]benzothiazole-3-carboxamide; N-(5-tetrazolyl)-7-amino-8-hydroxy-4-oxo-4H-pyrimido[2,1-b]benzothiazole-3-carboxamide; N-(5-tetrazolyl)-7-amino-8-chloro-4-oxo-4H-pyrimido[2,1-b]benzothiazole-3-carboxamide; and N-(5-tetrazolyl)-7-amino-8-fluoro-4-oxo-4H-pyrimido[2,1-b]benzothiazole-3-carboxamide.

EXAMPLE 19

N-(5-Tetrazolyl)-7-hydroxy-4-oxo-4H-pyrimido[2,1-b]benzothiazole-3-carboxamide

To a suspension of 3-carboxy-7-hydroxy-4-oxo-4H-benzo[2,1-b]benzothiazole (1.2 g.) in 50 ml. of dimethylformamide is added 827 mg. of 1,1'-carbonyldiimidazole and the reaction mixture warmed to 35° C. until the evolution of gas ceases. 5-Aminotetrazole (434 mg.) is added and the mixture heated at steam bath temperatures for 20 min. The suspension is cooled, filtered and the solids recrystallized from dimethylformamide.

EXAMPLE 20

The procedure of Example 19 is repeated, employing the appropriate starting reagents, to provide the following compounds:

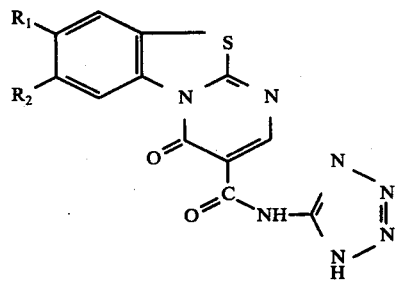

| $R_1$ | $R_2$ |
|---|---|
| HO- | HO- |
| HO- | $CH_3$- |
| HO- | $C_2H_5$- |
| HO- | F- |
| HO- | Cl- |
| HO- | $CH_3O$- |
| HO- | $n-C_3H_7O$- |
| HO- | $CH_3S$- |
| $CH_3$- | HO- |
| $i-C_3H_7$- | HO- |
| $CH_3O$- | HO- |
| $C_2H_5O$- | HO- |
| Cl- | HO- |
| F- | HO- |
| $CH_3S$- | HO- |
| $CF_3$- | HO- |

EXAMPLE 21

N-(5-Tetrazolyl)-7,8-diethoxy-4-oxo-4H-pyrimido[2,1-b]benzothiazole-3-carboxamide A slurry of 1.7 g. of 3-carboxy-4-oxo-4H-pyrimido[2,1-b]benzothiazole and 892 mg. of 1,1'-carbonyldiimidazole in 70 ml. of dimethylformamide is heated at steam bath temperatures for 10 min. To the hot reaction mixture is added 468 mg. of 5-aminotetrazole and the heating on the steam bath continued for 20 min. The suspension is cooled, filtered and the solids recrystallized from dimethylformamide, 1.1 g, m.p. > 300° C.

Anal. Calc'd. for $C_{16}H_{15}O_4N_7S$: C, 47.9; H, 3.8; N, 24.4. Found: C, 48.0; H, 3.8; N, 24.5.

EXAMPLE 22

N-(5-Tetrazolyl)-7,8-methylenedioxy-4-oxo-4H-pyrimido[2,1-b]benzothiazole-3-carboxamide In a manner similar to Example 21, 840 mg. of 3-carboxy-4-oxo-4H-pyrimido[2,1-b]benzothiazole, 535 mg. of 1,1'-carbonyldiimidazole and 281 mg. of 5-aminotetrazole in 35 ml. of dimethylformamide gives the desired product, which can be purified by recrystallization from dimethylformamide.

EXAMPLE 23

N-(5-Tetrazolyl)-7,8-ethylenedioxy-4-oxo-4H-pyrimido[2,1-b]benzothiazole-3-carboxamide Again, in a manner similar to Example 21, the desired product is prepared from 880 ml. of 3-carboxy-4-oxo-4H-pyrimido[2,1-b]benzothiazole, 535 mg. of 1,1'-carbonyldiimidazole and 281 mg. of 5-aminotetrazole in 40 ml. of dimethylformamide.

EXAMPLE 24

Injectable Preparation

One thousand grams of N-(5-tetrazolyl)-7-methoxy-4-oxo-4H-pyrimido[2,1-b]benzothiazole-3-carboxamide are intimately mixed and ground with 2500 grams of sodium ascorbate. The ground, dry mixture is placed in vials and sterilized with ethylene oxide after which the vials are sterilely stoppered. For intravenous administration, sufficient water is added to the materials in the vials to form a solution containing 5.0 mg. of active ingredient per milliter of injectable solution.

EXAMPLE 25

Tablets

A tablet base is prepared by blending the following ingredients in the proportion by weight indicated:

Sucrose, U.S.P.: 80.3
Tapioca Starch: 13.2
Magnesium Stearate: 6.5

Into this tablet base there is blended sufficient N-(5-tetrazolyl)-7-methoxy-4-oxo-4H-pyrimido[2,1-b]benzothiazole-3-carboxamide to provide tablets containing 20, 100, and 250 mg. of active ingredient per tablet. The compositions are each compressed into tablets, each weighing 360 mg., by conventional means.

EXAMPLE 26

Capsules

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient N-(5-tetrazolyl)-7,8-dimethoxy-4-oxo-4H-pyrimido[2,1-b]benzothiazole-3-carboxamide to provide capsules containing 10, 25 and 50 mg. of active ingredient per capsule. The compositions are filled into conventional hard gelatin capsules in the amount of 350 mg. per capsule.

In like manner, capsules containing 2.0 mg. and 6.0 mg. of active ingredient, and having 300 mg. of the following blends per capsule are prepared:

| Ingredients | Weight mg./capsule |
|---|---|
| Drug | 2.00 |
| N-methylglucamice | 18.00 |
| Lactose, anhydrous | 251.20 |
| Corn starch, anhydrous | 8.80 |

| Ingredients | Weight mg./capsule |
|---|---|
| Drug | 6.00 |
| N-methylglucamine | 18.00 |
| Lactose, anhydrous | 237.20 |
| Corn starch, anhydrous | 30.00 |
| *Talc | 8.80 |

*Talc added before encapsulation

EXAMPLE 27

Solution

A solution of N-(5-tetrazolyl)-7,8-dimethoxy-4-oxo-4H-pyrimido[2,1-b]benzothiazole-3-carboxamide is prepared with the following compositions:

Effective ingredient: 6.04 grams
Magnesium chloride hexahydrate: 12.36 grams
Monoethanolamine: 8.85 ml.
Propylene glycol: 376.00 grams
Water, distilled: 94.00 ml.

The resultant solution has a concentration of effective ingredient of 10 mg./ml. and is suitable for parenteral and, especially, for intramuscular administration.

EXAMPLE 28

Aerosol Suspension

A mixture of N-(5-tetrazolyl)-7,8-diethoxy-4-oxo-4H-pyrimido[2,1-b]benzothiazole-3-carboxamide (antiallergy agent) and the other ingredients under (a) in the examples below are micronized to a particle size of 1 to 5 microns in a ball mill. The resulting slurry is then placed in a container equipped with a valve and propellant (b) introduced by pressure filling through the valve nozzle to a gauge pressure of approximately 35–40 pounds per square inch at 20° C.

| Suspension A | | Percent |
|---|---|---|
| (a) | Antiallergy agent | 0.25 |
| | Isopropyl myristate | 0.10 |
| | Ethanol | 26.40 |
| (b) | 60–40% mixture of 1,2-dichlorotetrafluoro-ethane-1-chloropentafluoroethane | 73.25 |

| Suspension B | | |
|---|---|---|
| (a) | Antiallergy agent | 0.25 |
| | Ethanol | 26.50 |
| (b) | A 60–40% mixture of 1,2-dichlorotetrafluoroethane-1-chloropentafluoroethane | 73.25 |

What is claimed is:

1. A compound selected from the group consisting of:

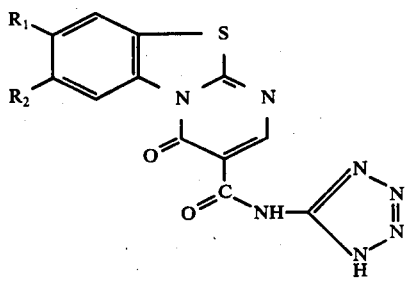

and a pharmaceutically acceptable base salt thereof wherein $R_1$ is selected from the group consisting of hydrogen, alkyl having from 1 to 3 carbon atoms, alkoxy having from 1 to 3 carbon atoms, hydroxy, chloro, fluoro, trifluoromethyl, nitro, amino and methylthio; $R_2$ is selected from the group consisting of hydrogen, alkyl having from 1 to 3 carbon atoms, alkoxy having from 1 to 3 carbon atoms, hydroxy, chloro, fluoro and methylthio; and $R_1$ and $R_2$ when taken together are selected from the group consisting of methylenedioxy and ethylenedioxy.

2. A compound of claim 1 wherein $R_1$ is alkoxy having from 1 to 3 carbon atoms.

3. The compound of claim 2 wherein $R_1$ and $R_2$ are each methoxy.

4. The compound of claim 2 wherein $R_1$ and $R_2$ are each ethoxy.

5. A compound of claim 1 wherein $R_1$ is hydrogen.

6. The compound of claim 5 wherein $R_1$ is methoxy.

7. The compound of claim 5 wherein $R_1$ is fluoro.

8. The compound of claim 5 wherein $R_1$ is hydrogen.

9. A method of inhibiting the release of mediators of anaphylaxis in mammals and thereby reducing bronchoconstriction covered by said mediators, said method which comprises oral, intraperitoneal or inhalation administration to a mammal an amount of a compound which inhibits release of said mediators, said compound being selected from the group consisting of

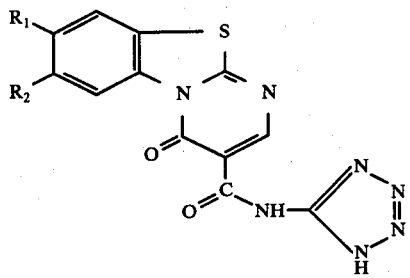

and a pharmaceutically acceptable base salt thereof wherein $R_1$ is selected from the group consisting of hydrogen, alkyl having from 1 to 3 carbon atoms, alkoxy having from 1 to 3 carbon atoms, hydroxy, chloro, fluoro, trifluoromethyl, nitro, amino and methylthio; $R_2$ is selected from the group consisting of hydrogen, alkyl having from 1 to 3 carbon atoms, alkoxy having from 1 to 3 carbon atoms, hydroxy, chloro, fluoro and methylthio; and $R_1$ and $R_2$ when taken together are selected from the group consisting of methylenedioxy and ethylenedioxy.

10. The method of claim 9 wherein $R_1$ is alkoxy having from 1 to 3 carbon atoms.

11. The method of claim 10 wherein $R_1$ and $R_2$ are each methoxy.

12. The method of claim 10 wherein $R_1$ and $R_2$ are each ethoxy.

13. The method of claim 9 wherein $R_2$ is hydrogen.

14. The method of claim 13 wherein $R_1$ is methoxy.

15. The method of claim 13 wherein $R_1$ is fluoro.

16. The method of claim 13 wherein $R_1$ is hydrogen.

* * * * *